United States Patent
Cottone, Jr. et al.

(10) Patent No.: US 8,419,786 B2
(45) Date of Patent: *Apr. 16, 2013

(54) SELF-EXPANDING STENT

(75) Inventors: Robert John Cottone, Jr., Fort Lauderdale, FL (US); Gary Jay Becker, Maimi, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 103 days.

This patent is subject to a terminal disclaimer.

(21) Appl. No.: 11/668,869

(22) Filed: Jan. 30, 2007

(65) Prior Publication Data

US 2008/0147159 A1 Jun. 19, 2008

Related U.S. Application Data

(63) Continuation of application No. 09/862,690, filed on May 22, 2001, now Pat. No. 7,169,175.

(60) Provisional application No. 60/206,211, filed on May 22, 2000.

(51) Int. Cl.
*A61F 2/06* (2006.01)

(52) U.S. Cl.
USPC .......................... 623/1.22; 623/1.2

(58) Field of Classification Search ................. 623/1.22, 623/1.11, 1.15, 1.2
See application file for complete search history.

(56) References Cited

U.S. PATENT DOCUMENTS

| | | | |
|---|---|---|---|
| 3,868,956 A | 3/1975 | Alfidi et al. | |
| 4,503,569 A | 3/1985 | Dotter | |
| 4,505,767 A | 3/1985 | Quin | |
| 4,665,906 A | 5/1987 | Jervis | |
| 4,795,458 A | 1/1989 | Regan | |
| 4,820,298 A | 4/1989 | Leveen et al. | |

(Continued)

FOREIGN PATENT DOCUMENTS

| | | |
|---|---|---|
| EP | 0565251 | 10/1993 |
| EP | 0645125 | 3/1995 |

(Continued)

*Primary Examiner* — Gary Jackson
*Assistant Examiner* — Kevin Everage
(74) *Attorney, Agent, or Firm* — White & Case LLP

(57) ABSTRACT

The stent of this invention is a self-expanding stent created by a scaffolding lattice. The stent may be made from a nickel-titanium alloy. The lattice is formed from two different types of helices that proceed circumferentially in opposite directions along the longitudinal axis of the stent. The helices have no free ends. The first type of helix is formed by a series of undulations and the second type of helix is formed from a series of connection elements. The undulations may be in a zigzag or sinusoidal pattern. The connection elements connect the junction points lying on adjacent turns of the first type of helix. The junction points are formed by the ascending and descending arms of the undulations or zigzags. The ends of the stent may be formed by a closed circumferential element which is linked by connection elements to a transition zone. The transition zone is formed by a closed loop that connects directly to the first helix. The amplitude of the undulations or zigzags forming the transition zone increases from the closed loop to the point connecting the transition zone with the first type of helix. The closed circumferential element may be made from a radiopaque material. The scaffolding lattice design of the stent provides a stent having a high degree of flexibility as well as radial strength.

32 Claims, 18 Drawing Sheets

U.S. PATENT DOCUMENTS

| | | |
|---|---|---|
| 4,921,479 A | 5/1990 | Grayzel |
| 4,990,155 A | 2/1991 | Wilkoff |
| 5,037,427 A | 8/1991 | Harada et al. |
| 5,067,957 A | 11/1991 | Jervis |
| 5,071,407 A | 12/1991 | Termin et al. |
| 5,108,420 A | 4/1992 | Marks |
| 5,133,732 A | 7/1992 | Wiktor |
| 5,163,952 A | 11/1992 | Froix |
| 5,190,546 A | 3/1993 | Jervis |
| 5,197,978 A | 3/1993 | Hess |
| 5,201,901 A | 4/1993 | Harada et al. |
| 5,217,483 A | 6/1993 | Tower |
| 5,224,953 A | 7/1993 | Morgentaler |
| 5,226,913 A | 7/1993 | Pinchuk |
| 5,231,989 A | 8/1993 | Middleman et al. |
| 5,242,451 A | 9/1993 | Harada et al. |
| 5,258,020 A | 11/1993 | Froix |
| 5,304,200 A | 4/1994 | Spaulding |
| 5,345,937 A | 9/1994 | Middleman et al. |
| 5,354,308 A | 10/1994 | Simon et al. |
| 5,354,309 A | 10/1994 | Schnepp-Pesch et al. |
| 5,370,608 A | 12/1994 | Sahota et al. |
| 5,378,239 A | 1/1995 | Termin et al. |
| 5,417,653 A | 5/1995 | Sahota et al. |
| 5,433,723 A | 7/1995 | Lindenberg et al. |
| 5,449,373 A | 9/1995 | Pinchasik |
| 5,466,242 A | 11/1995 | Mori |
| 5,477,864 A | 12/1995 | Davidson |
| 5,496,277 A | 3/1996 | Termin et al. |
| 5,498,227 A | 3/1996 | Mawad |
| 5,514,154 A | 5/1996 | Lau et al. |
| 5,540,701 A | 7/1996 | Sharkey et al. |
| 5,545,210 A | 8/1996 | Hess et al. |
| 5,562,641 A | 10/1996 | Flomenblit et al. |
| 5,562,697 A | 10/1996 | Christiansen |
| 5,562,730 A | 10/1996 | Davidson |
| 5,569,295 A | 10/1996 | Lam |
| 5,603,721 A | 2/1997 | Lau et al. |
| 5,609,627 A | 3/1997 | Goicoechea et al. |
| 5,628,788 A | 5/1997 | Pinchuk |
| 5,683,450 A | 11/1997 | Goicoechea et al. |
| 5,693,086 A | 12/1997 | Goicoechea et al. |
| 5,695,516 A | 12/1997 | Fischell et al. |
| 5,707,386 A | 1/1998 | Schnepp-Pesch et al. |
| 5,725,572 A | 3/1998 | Lam et al. |
| 5,733,303 A | 3/1998 | Israel et al. |
| 5,776,161 A | 7/1998 | Globerman |
| 5,800,515 A | 9/1998 | Nadal et al. |
| 5,800,520 A | 9/1998 | Fogarty et al. |
| 5,807,398 A | 9/1998 | Shaknovich |
| 5,810,872 A | 9/1998 | Kanesaka et al. |
| 5,824,043 A * | 10/1998 | Cottone, Jr. .................. 623/1.13 |
| 5,824,058 A | 10/1998 | Ravenscroft et al. |
| 5,827,321 A | 10/1998 | Roubin et al. |
| 5,843,120 A | 12/1998 | Israel et al. |
| 5,843,164 A | 12/1998 | Frantzen et al. |
| 5,843,175 A | 12/1998 | Frantzen |
| 5,846,246 A | 12/1998 | Dirks et al. |
| 5,860,998 A | 1/1999 | Robinson et al. |
| 5,860,999 A | 1/1999 | Schnepp-Pesch et al. |
| 5,868,782 A | 2/1999 | Frantzen |
| 5,879,381 A | 3/1999 | Moriuchi et al. |
| 5,913,896 A | 6/1999 | Boyle et al. |
| 5,913,897 A * | 6/1999 | Corso et al. .................. 623/1.15 |
| 5,925,061 A * | 7/1999 | Ogi et al. ....................... 623/1.2 |
| 5,931,866 A | 8/1999 | Frantzen |
| 5,938,696 A | 8/1999 | Goicoechea et al. |
| 5,948,017 A | 9/1999 | Taheri |
| 5,976,153 A | 11/1999 | Fischell et al. |
| 5,980,532 A | 11/1999 | Wang |
| 6,001,123 A | 12/1999 | Lau |
| 6,013,854 A | 1/2000 | Moriuchi |
| 6,022,374 A | 2/2000 | Imran |
| 6,042,597 A * | 3/2000 | Kveen et al. .................. 623/1.15 |
| 6,042,606 A | 3/2000 | Frantzen |
| 6,063,113 A | 5/2000 | Kavteladze et al. |
| 6,083,259 A | 7/2000 | Frantzen |
| 6,203,569 B1 | 3/2001 | Wijay |
| 6,309,414 B1 | 10/2001 | Rolando et al. |
| 6,312,459 B1 | 11/2001 | Huang et al. |
| 6,315,794 B1 | 11/2001 | Richter |
| 6,348,065 B1 * | 2/2002 | Brown et al. ................. 623/1.16 |
| 6,352,552 B1 * | 3/2002 | Levinson et al. ............ 623/1.15 |
| 6,423,091 B1 | 7/2002 | Hojeibane |
| 6,551,351 B2 | 4/2003 | Smith et al. |
| 7,169,175 B2 * | 1/2007 | Cottone et al. ............... 623/1.22 |
| 7,169,175 C1 | 6/2009 | Cottone et al. |
| 2003/0167084 A1 | 9/2003 | Orlowski |

FOREIGN PATENT DOCUMENTS

| | | |
|---|---|---|
| EP | 0801934 | 10/1997 |
| EP | 0807424 | 11/1997 |
| GB | 2281865 | 3/1995 |
| WO | WO 93/13824 | 7/1993 |
| WO | WO 94/12136 | 6/1994 |
| WO | WO 95/14500 | 8/1995 |
| WO | WO 95/23564 | 9/1995 |
| WO | WO 96/19953 | 7/1996 |
| WO | WO 96/26689 | 9/1996 |
| WO | WO 97/21399 | 6/1997 |
| WO | WO 97/40780 | 11/1997 |

* cited by examiner

SELF-EXPANDING STENT

This application is a continuation of application No. 09/862,690, filed May 22, 2001, U.S. Pat. No. 7,169,175, which claims the benefit of U.S. Provisional Application No. 60/206,211, filed May 22, 2000.

FIELD OF THE INVENTION

The present invention relates to flexible stents that are implanted in a lumen in the body and in particular in blood vessels.

BACKGROUND OF THE INVENTION

Stents are scaffolds which are positioned in diseased vessel segments to support the vessel walls. Stents are used in angioplasty to repair and reconstruct blood vessels. Placement of a stent in the affected arterial segment prevents elastic recoil and closing of the artery. Stents also prevent local dissection of the artery along the medial layer of the artery. Stents may be used inside the lumen of any physiological space, such as an artery, vein, bile duct, urinary tract, alimentary tract, tracheobronchial tree, cerebral aqueduct or genitourinary system. Stents may also be placed inside the lumen of human as well as non-human animals.

In general there are two types of stents: radially, self-expanding and radially, balloon-expandable. The balloon-expandable stent is placed in a diseased segment of a vessel by inserting an unexpanded stent into the affected area within the vessel The stent is expanded by positioning a balloon inside the stent and inflating the balloon to expand the stent. Inflation remodels the arterial plaque and secures the stent within the affected vessel. One problem with balloon stents is that the inside diameter of the stent may become smaller over time if the stent lacks expanding resilience. The result of this lack of resilience is that the stent collapses due to the natural elastic recoil of the blood vessel.

In contrast, a self-expanding stent is capable of expanding by itself There are many different designs of self-expanding stents, including, coil (spiral), circular, cylinder, roll, stepped pipe, high-order coil, cage or mesh. Self-expanding stents are formed from super-elastic metal. See, for example, U.S. Pat. No. 6,013,854 to Moriuchi. The self-expanding stent is placed in the vessel by inserting the stent in a compressed state into the affected region, e.g., an area of stenosis. Once the compressive force is removed, the stent expands to fill the lumen of the vessel. The stent may be compressed using a tube that has a smaller outside diameter than the inner diameter of the affected vessel region. When the stent is released from confinement in the tube, the stent expands to resume its original shape and becomes securely fixed inside the vessel against the vessel wall.

Each of the various stent designs that have been used with self-expanding stents has certain functional problems. For example, a stent formed in the shape of a simple circular cylinder does not compress easily. Consequently, insertion of the stent into the affected region of a vessel may be very difficult.

One approach of the prior art stent designs to overcome this problem is to provide a stent formed by zigzag elements as disclosed in U.S. Pat. No. 5,562,697 to Christiansen. A stent formed from a zigzag pattern has flexibility in the axial direction to facilitate delivery of the stent, however, this type of stent often lacks sufficient radial strength to maintain patentcy of the vessel after elastic recoil.

In order to provide increased radial strength of the zigzag design, the zigzag elements may be connected with connection elements. U.S. Pat. No. 6,042,597 to Kveen et al. describes a balloon expandable stent formed by a continuous helical element having undulating portions which form peaks and troughs where all of the peaks of adjacent undulating portions are connected by curvilinear elements. Connection elements between each adjacent undulating portion may impair flexibility of the stent.

Another approach is to provide a plurality of interconnecting cells which are in the shape of a diamond or rhomboid as in U.S. Pat. No. 6,063,113 to Karteladze et al. or U.S. Pat. No. 6,013,584 to Moriuchi. This type of stent has cells which rigidly interlock. Consequently, these types of stents have a comparatively high degree of rigidity and do not bend to accommodate changes in vessel shape.

It will be appreciated that in spite of these disclosures, there is still a great need for a self-expanding stent that overcomes the deficiencies of the prior art stents. Accordingly, the present invention provides a geometric design for a stent that has both a high degree of flexibility and significant radial strength. The design of this stent also allows it to be inserted into small diameter vessels. The stent is further able to respond dynamically to changes in blood pressure.

SUMMARY OF THE INVENTION

The stent of the invention comprises a self-expanding stent formed from a scaffolding lattice. The stent may be made of a nickel-titanium alloy. The lattice comprises two different types of helices forming a hollow tube which has no free ends. The first type of helix is formed from a plurality of undulations and the second type of helix is formed from a plurality of connecting elements such that the connection elements connect fewer than all of the undulations in adjacent turns of the first helix. The first and second helix proceed circumferentially in opposite directions along the longitudinal axis of the hollow tube. Each undulation is formed from ascending and descending arms connected together at a junction point. The connection element may extend between the junction points lying on adjacent undulations.

In one embodiment, the ends of the stent are formed by a closed circumferential element formed from a plurality of undulations linked by a plurality of connection elements to a transition zone. The transition zone is formed by a plurality of undulations creating a closed loop at one end of the transition zone. The undulations of the transition zone are connected to the undulations which form the first type of helix at the other end of the transition zone. The two ends, the closed loop and the connection between the undulations of the transition zone and the first type of helix, are separated by at least one 360 degree turn. The amplitude of the undulations forming the transition zone increases as the undulations proceed circumferentially from the end forming the closed loop to the end connected to the first helix. The closed circumferential element may be radiopaque.

In another embodiment, the stent comprises a scaffolding lattice having two different types of helices forming a hollow tube having no free ends. The first type of helix is formed from a plurality of zigzags and the second type of helix is formed from a plurality of connecting elements wherein the connection elements connect fewer than all of the zigzags in adjacent turns of the first type of helix. The first and second types of helices proceed circumferentially in opposite directions along the hollow tube. Each zigzag is formed from ascending and descending arms connected together at a junction point. The connection element can extend between the junction points lying on adjacent zigzags.

The ends of the stent may be formed by a closed circumferential element formed from a plurality of zigzags linked by a plurality of connection elements to a transition zone. In this embodiment, the zigzags are formed by a plurality of zigzags having a closed loop at one end. At the other end, the zigzags connect to the zigzags forming the first helix. The two ends of the transition zone are separated by at least one 360 degree turn. The amplitude of the zigzags forming the transition zone increases as the zigzags proceed circumferentially from the end forming the closed loop to the end connected to the first helix.

In a third embodiment, the self-expanding stent comprises at least one continuous first helical element having no free ends. The first helical element is formed from a plurality of zigzags. The second helical element is formed from a plurality of connection elements such that the connection elements connect fewer than all of the zigzags in adjacent turns of the first helix. Both the first and second helix proceed circumferentially in opposite directions to form a scaffolding lattice in a tubular shape. The connection elements connect two peaks lying on adjacent zigzags.

DETAILED DESCRIPTION OF THE INVENTION

The present invention relates to a self-expanding stent. A stent means any medical device which when inserted into the lumen of a vessel expands the cross-sectional lumen of that vessel. The stent of the invention may be deployed in any artery, vein, duct or other vessel such as a ureter or urethra. The stents may be used to treat narrowing or stenosis of any artery, including, the coronary, infrainguinal, aortoiliac, subclavian, mesenteric or renal arteries.

The term "undulation" refers to the bends in elements forming the first type of helix in the stent. Undulations may be formed in a sinusoidal, zigzag pattern or similar geometric pattern.

The stent comprises a hollow cylindrical member having no free ends and a wall surface. The wall may have a substantially uniform thickness. In the compressed state, the stent has a first diameter. This compressed state may be achieved using a mechanical compressive force. The compressed state permits intraluminal delivery of the stent into a vessel lumen. The compressive force may be exerted by means of a sheath in which the compressed stent is placed. In the uncompressed state, the stent has a second variable diameter which it acquires after withdrawal of the compressive force such as that applied by the sheath. Upon withdrawal of the compressive force, the stent immediately expands to provide structural support for the vessel.

The stent is formed from a hollow tube made of super elastic metal. Notches or holes are made in the tube forming the elements of the stent. The notches and holes can be formed in the tube by use of a laser, e.g., a YAG laser, electrical discharge, chemical etching or mechanical cutting. As a result of this type of processing, the stent comprises a single piece that lacks any abrupt change in the physical property of the stent such as that which would result from welding. The formation of the notches and holes to prepare the claimed stent is considered within the knowledge of a person of ordinary skill in the art.

The wall of the stent comprises a scaffolding lattice, where the lattice is formed from two different types of helices. The stent is a hollow tube that has no free ends. The scaffolding lattice uniformly supports the vessel wall while maintaining deployed flexibility. This design further allows the stent to conform to the shape of the vessel. The first type of helix is formed from a plurality of zigzag elements continuously linked together and the second type of helix is formed from a plurality of connection elements in series with the zigzag elements. The connection elements connect fewer than all of the zigzags in adjacent turns of the first type of helix. The first and second types of helices proceed circumferentially in opposite directions along the longitudinal axis of the hollow tube.

Figure 12:
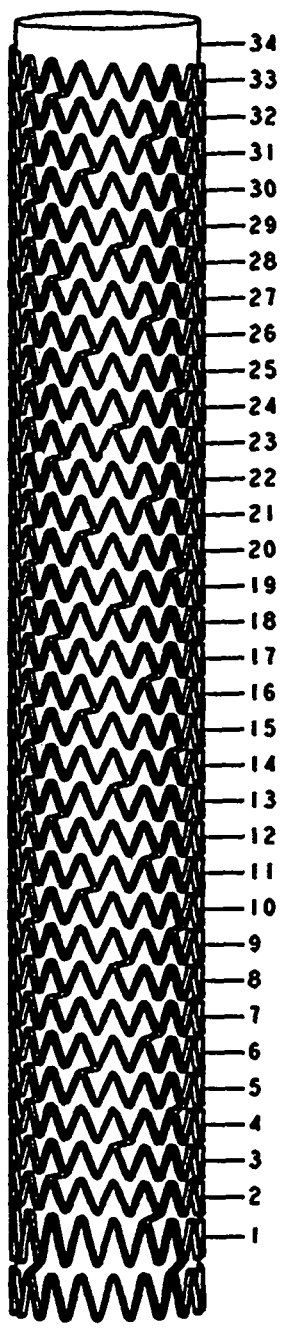

FIG. 12 shows a three-dimensional side-perspective view of the claimed stent. One part of the scaffolding lattice is formed from a first type of helix composed of a plurality of zigzag elements. The features of this type of helix are shown as numbers 1-33. Each number represents one 360-degree turn of the helix formed by the zigzag elements. Adjacent turns of the helix are formed by the zigzag elements. The following lists the pairs of adjacent turns illustrated in FIG. 12: 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, and 33-34. Number 34 represents the lumen of a blood vessel where the stent has been placed.

Figure 13:
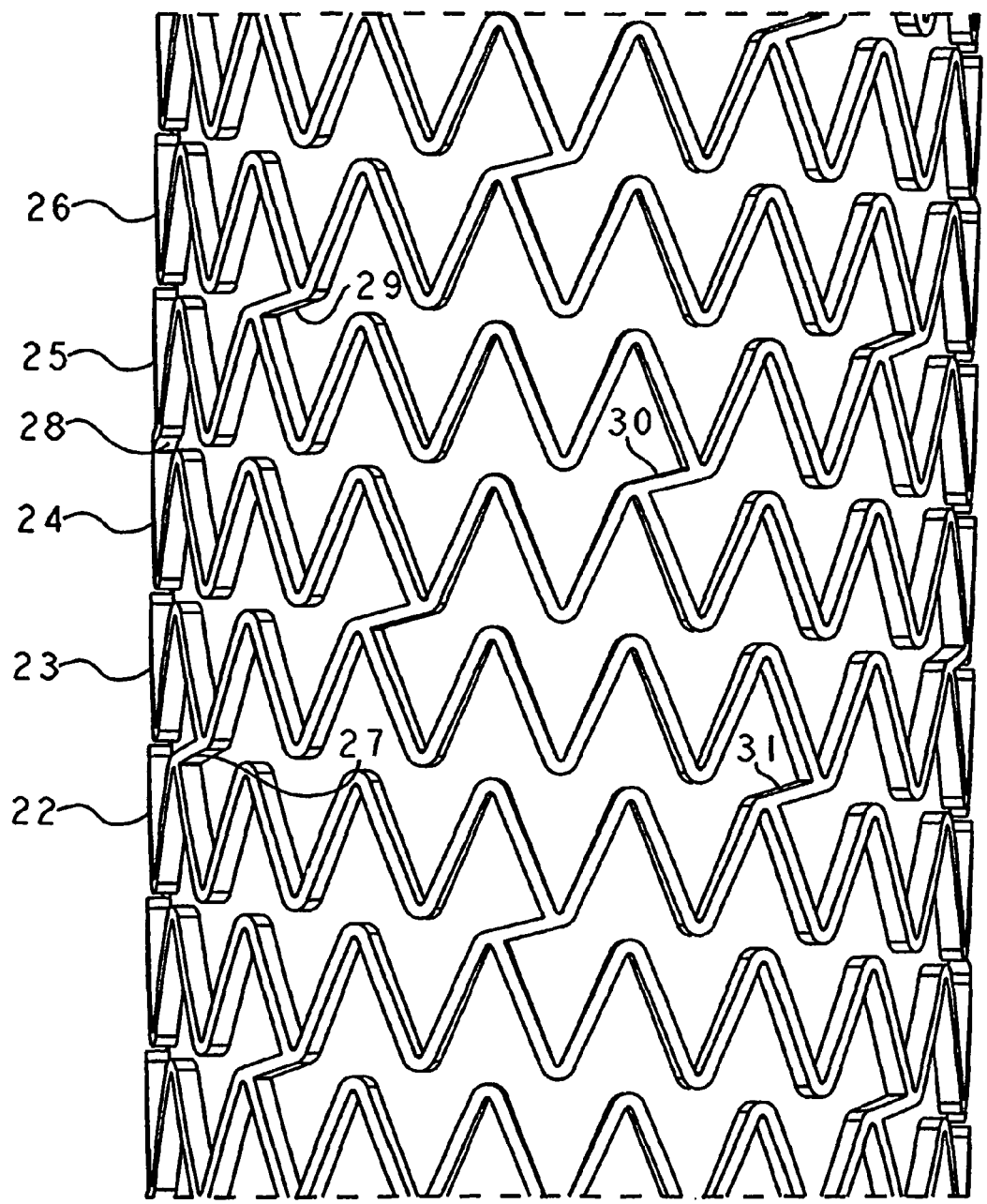

The second type of helix is formed by the connection elements. Adjacent turns of the helix formed by the zigzag elements are connected by at least one connection element. These connection elements are illustrated in FIG. 13, which shows a close-up side-perspective view of the stent illustrated in FIG. 12. Adjacent turns of the helix are formed by the zigzag elements and are listed as follows in FIG. 13: 22-23, 23-24, 24-25 and 25-26. The adjacent turns are connected by connection elements positioned at an angle not parallel to the longitudinal axis of the stent. For example, adjacent turns 22 and 23 are connected by connection elements 27 and 31; adjacent turns 24 and 25 are connected by connection elements 28 and 30; and adjacent elements 25 and 26 are connected by connection element 29. The number of connection elements connecting two adjacent turns of the helix formed by the zigzag elements varies from two in each 360-degree turn of the first type of helix to four in each 360-degree turn. In some embodiments, the number of connection elements may be greater than four. In all embodiments, the number of connection elements connecting adjacent turns of the helix is less than the number of zigzags in one 360-degree turn of the helix.

Figure 14:
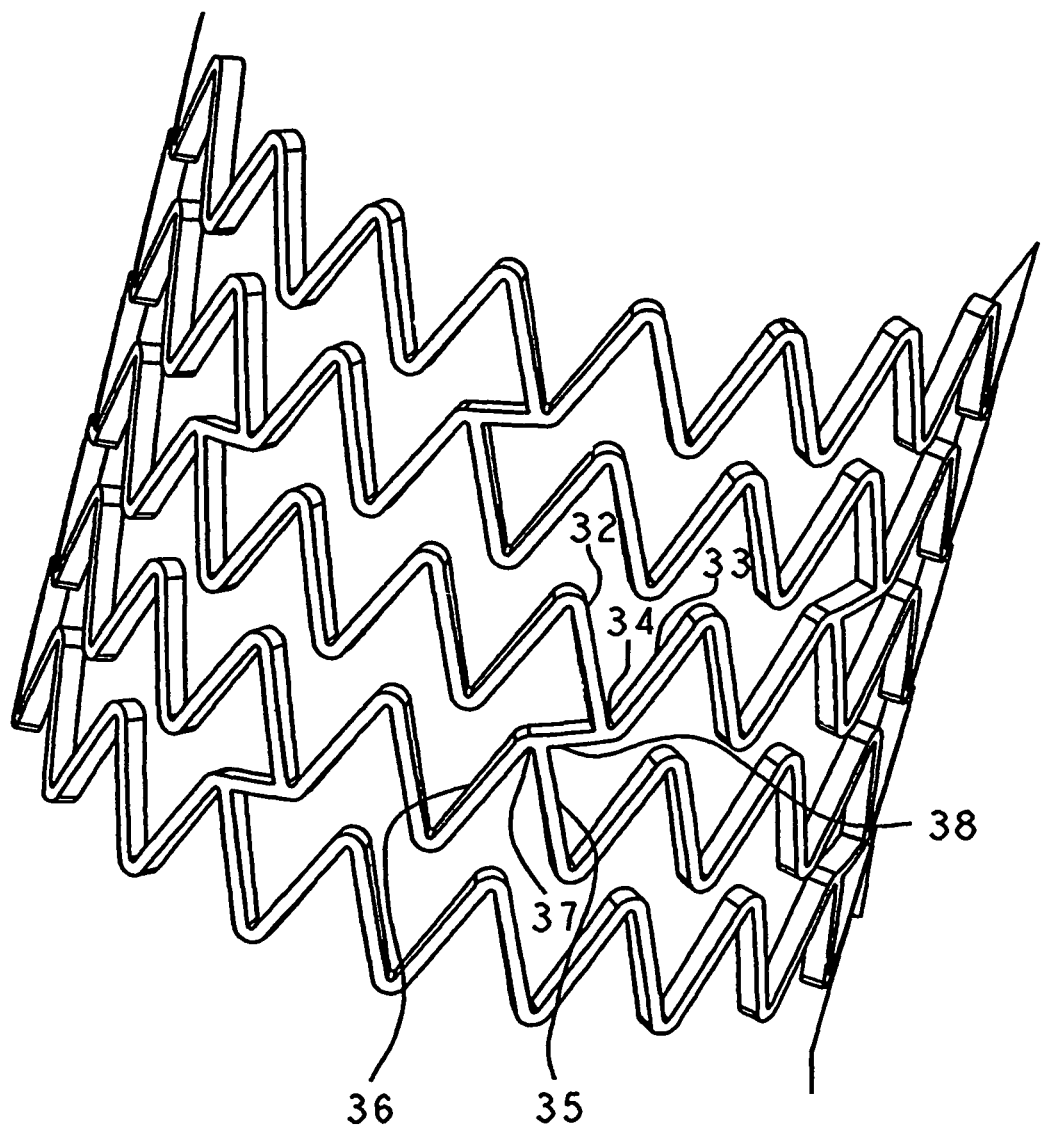

Zigzag elements are formed by ascending and descending arms having a junction point. This is illustrated in FIG. 14, which shows an enlarged side-perspective view of several zigzag elements The ascending and descending arms of one zigzag element in one turn of the helix formed by the zigzag elements are shown as 32 and 33, respectively, and the ascending and descending arms of a zigzag in an adjacent turn of the helix are shown as 35 and 36, respectively. Each of the zigzag elements is connected at a junction point, 34 and 37, by a connection element 38.

Figure 15:
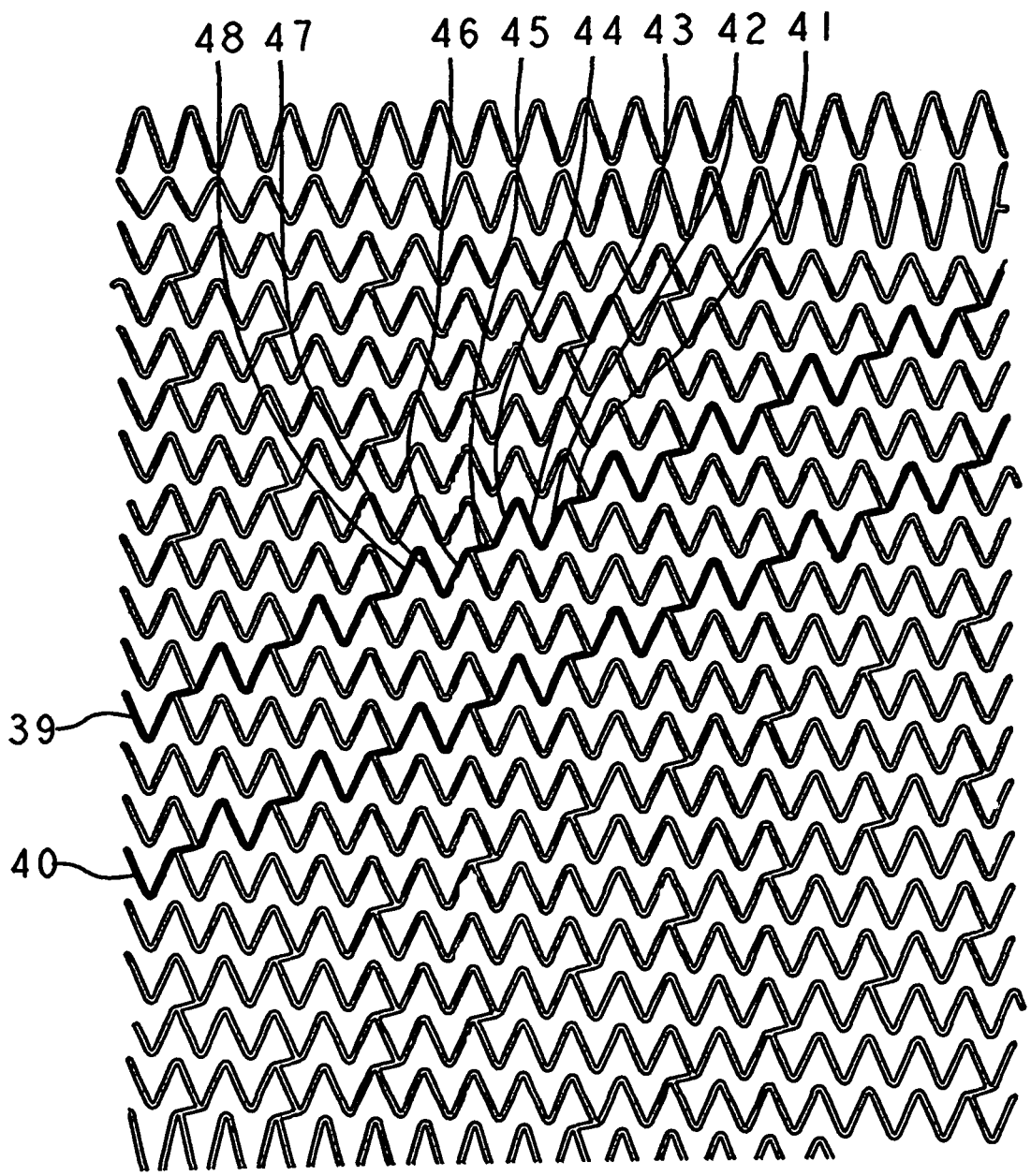

Thus, as illustrated by FIGS. 12 through 14, the scaffolding lattice of the stent is formed by two different types of helices. The first type of helix is formed from the zigzag elements. The second type of helix is formed by the connection elements. This type of helix is further illustrated in FIG. 15, which shows a flattened perspective of the stent where the tube of the stent has been cut down the longitudinal axis of the tube and laid flat. Two helical elements formed by the connective elements 39 and 40 are shown by highlighting in FIG. 15. The helical element formed by the connection elements comprises in series a connection element 41 linked directly to the descending 42, ascending 43 and descending 44 arms of the zigzag elements. The descending arm 44 is then linked to connection element 45 which in turn is linked to the descending 46, ascending 47 and descending 48 arms of the zigzag elements. This pattern is repeated throughout the body of the stent forming the second type of helix. The number of helices formed by the connection elements is determined by the number of connection elements connecting adjacent turns. The flexibility of the stent in a compressed as well as in a deployed state may be altered by varying the number of connection elements in each 360-degree turn of the helix formed by the zigzag elements. In general, the fewer the number of connection elements in each 360-degree turn of the helix formed by the zigzag elements the more flexible the stent and conversely the greater the number of connection elements in each 360-degree turn of the helix formed by the zigzag elements, the more rigid the stent. In contrast, the stent described in U.S. Pat. No. 6,042,597 to Kveen et al. has connection elements connecting every peak in adjacent undulations rendering it comparatively rigid.

Figure 16:
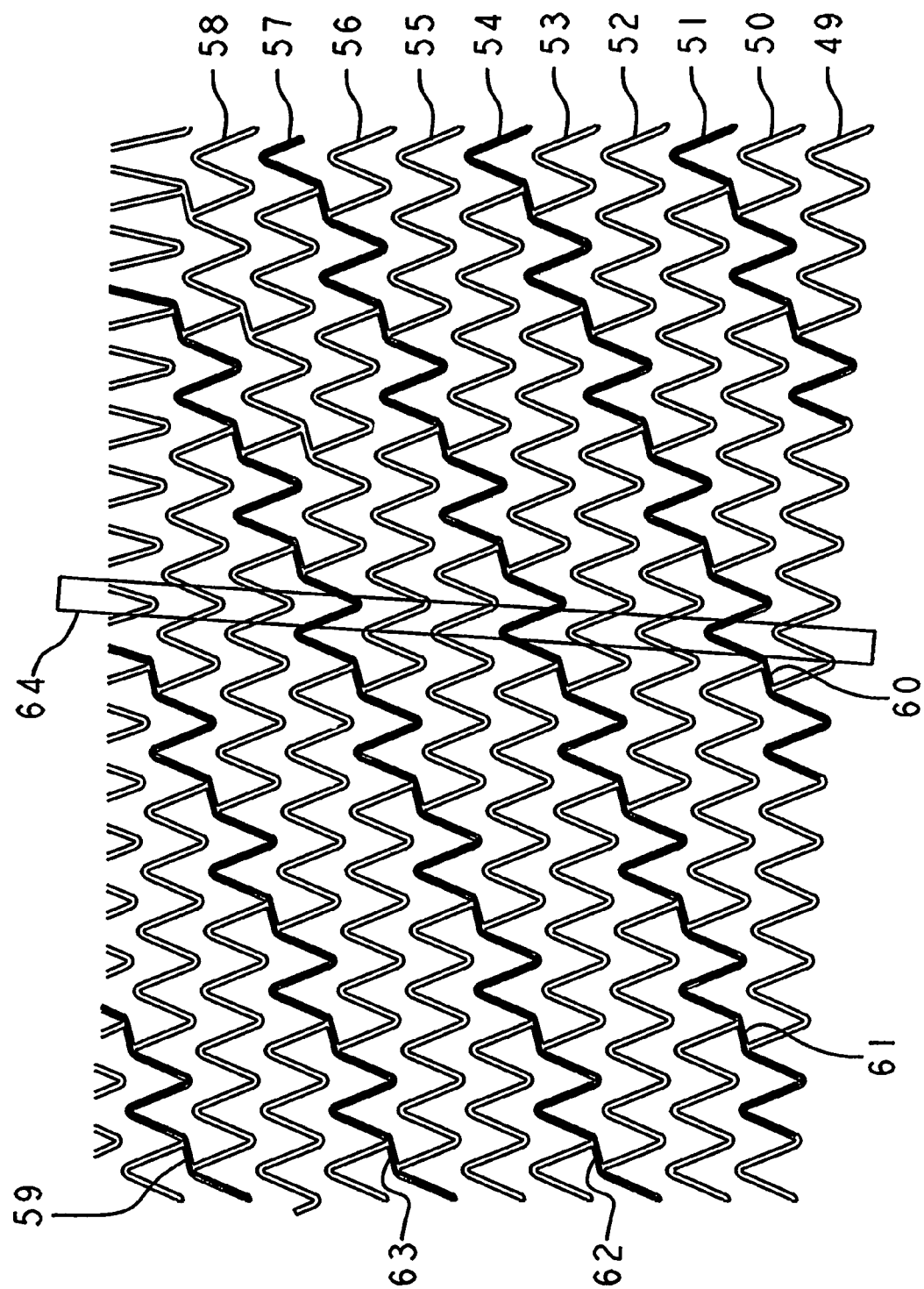

In FIG. 16, the scaffolding lattice is illustrated in a flattened perspective where the tube of the stent has been cut down the longitudinal axis and the stent laid flat. The figure shows only a portion of the body of the stent. The helix formed by the zigzag elements is shown as 49-58 and the helix formed by the connection elements in series with the zigzag elements is shown as 59-63. The helix formed by the zigzag elements 49-58 proceeds circumferentially in an opposite direction along the longitudinal axis of the stent 64 from the helix formed by the connection elements in series with the zigzag elements 59-63.

Figure 17:
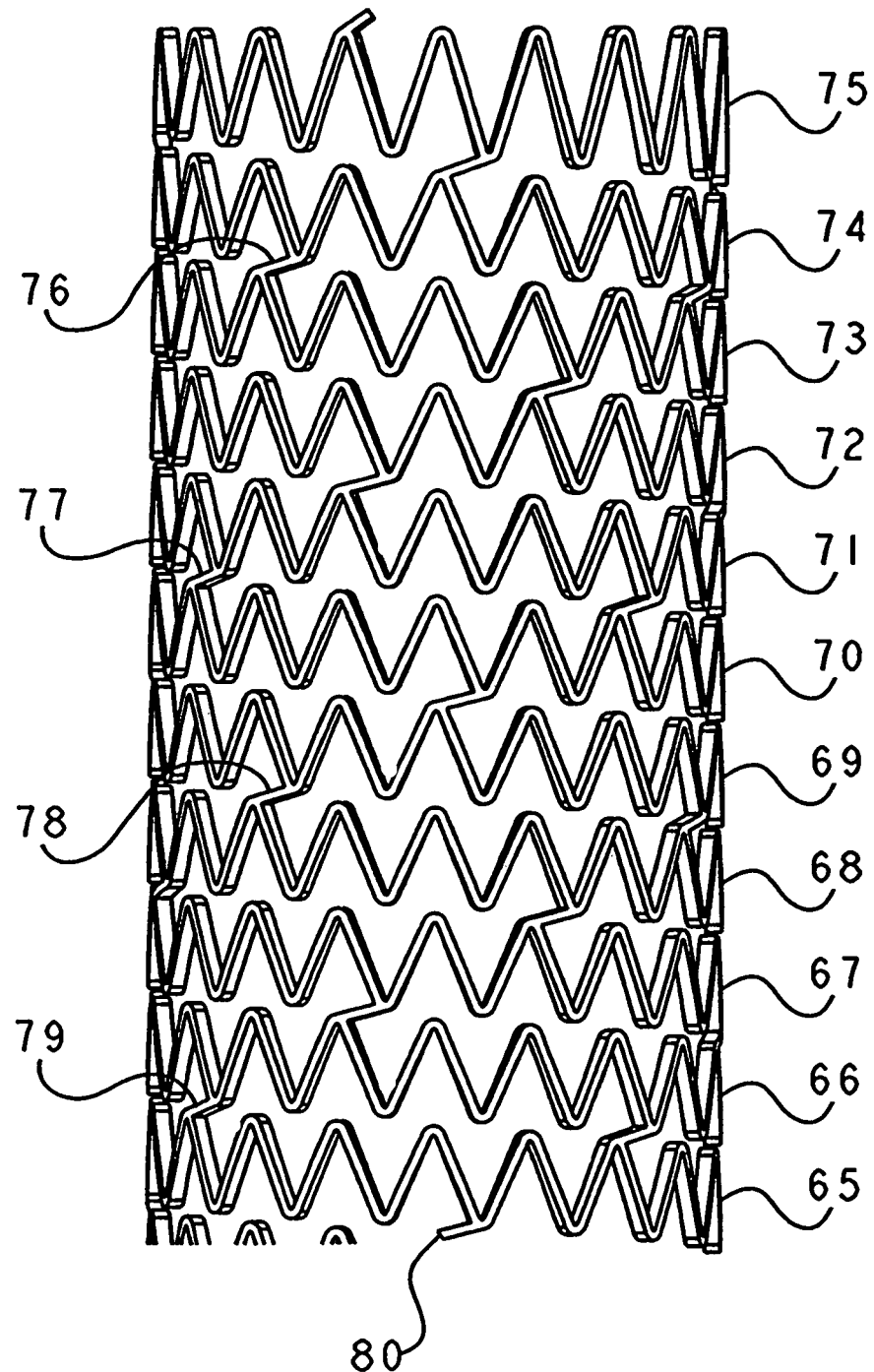

The scaffolding lattice formed by the two different types of helices is further illustrated in FIG. 17, which shows a three-dimensional side perspective of the stent. The helix formed by the plurality of zigzag elements is shown as 65-75. The helix formed by the connection elements in series with the zigzag elements is shown as 76-80. Together, the two different types of helices form the scaffolding lattice.

Figure 18:
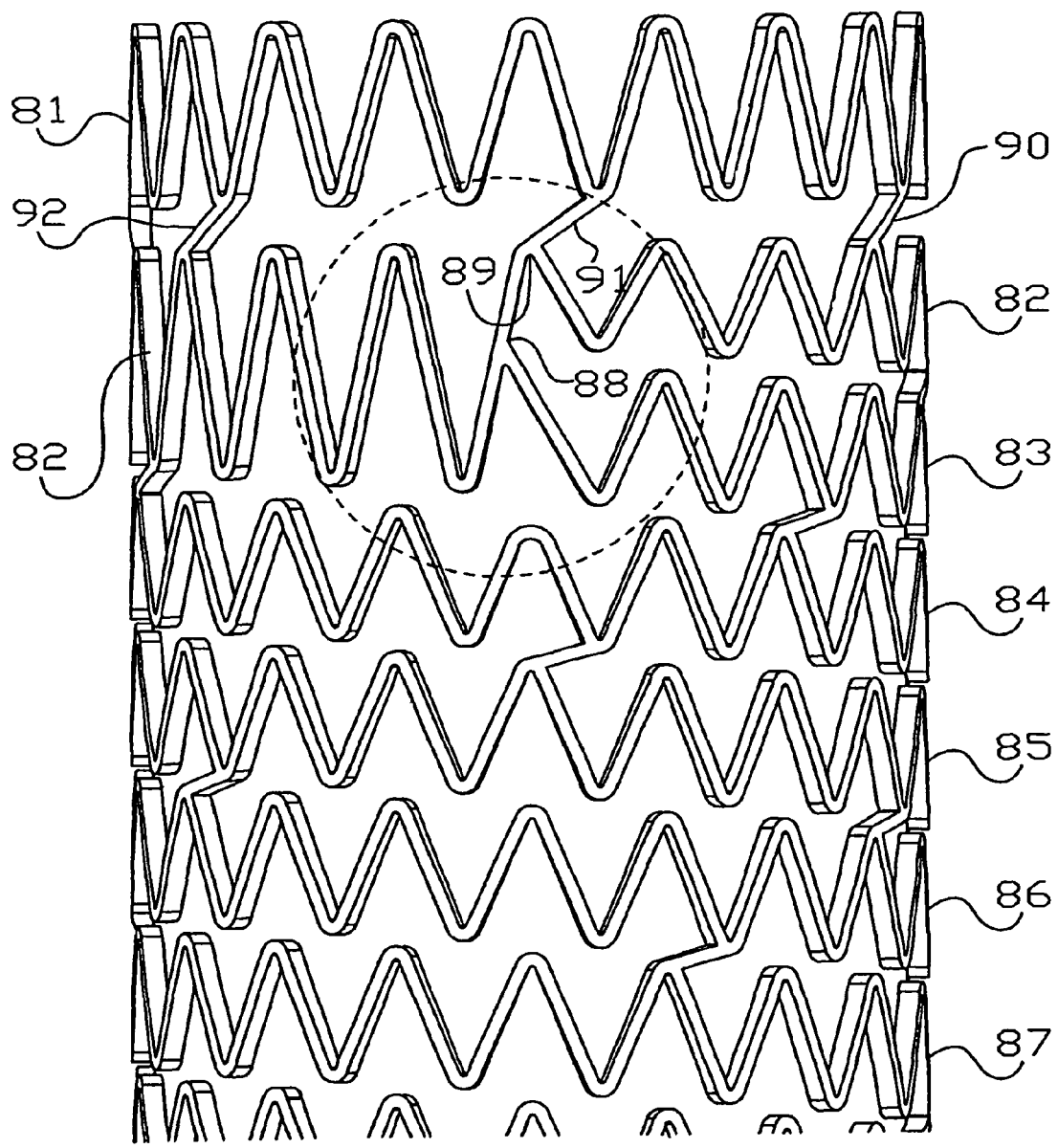

The ends of the stent may be formed by a closed circumferential element 81 composed of a plurality of zigzags linked by a plurality of connection elements 90-92 to a transition zone 82. The closed circumferential element and the transition zone are illustrated in FIG. 18. The transition zone 82 is formed by a plurality of zigzags which form a closed loop at one end 89 and connect to the helix formed by the continuous zigzags 83-87 at the other end 88. The two ends of the zigzag elements forming the transition zone are separated by at least one 360-degree turn of the helix formed by the zigzag elements. The amplitude of the zigzags forming the transition zone increases as the zigzags proceed circumferentially from the end forming the closed loop 89 to the end connected to the first type of helix 88. The closed circular circumferential element may be radiopaque as described in U.S. Pat. No. 6,022,374 to Imran, incorporated herein ih its entirety by reference.

In another embodiment, the transition zone may be used to link two stent segments having different internal diameters, where one segment is linked directly to the transition zone and the other segment is linked by connection elements to the other segment. This type of design allows the stent to conform to anatomical vessels having different diameters.

Figure 1:
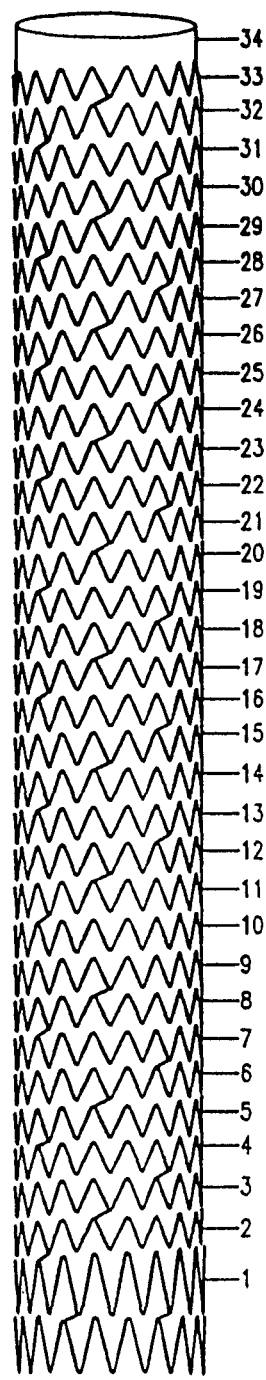
FIGS. 1 and 12 show three-dimensional side-perspective views of the stent.
Figure 2:
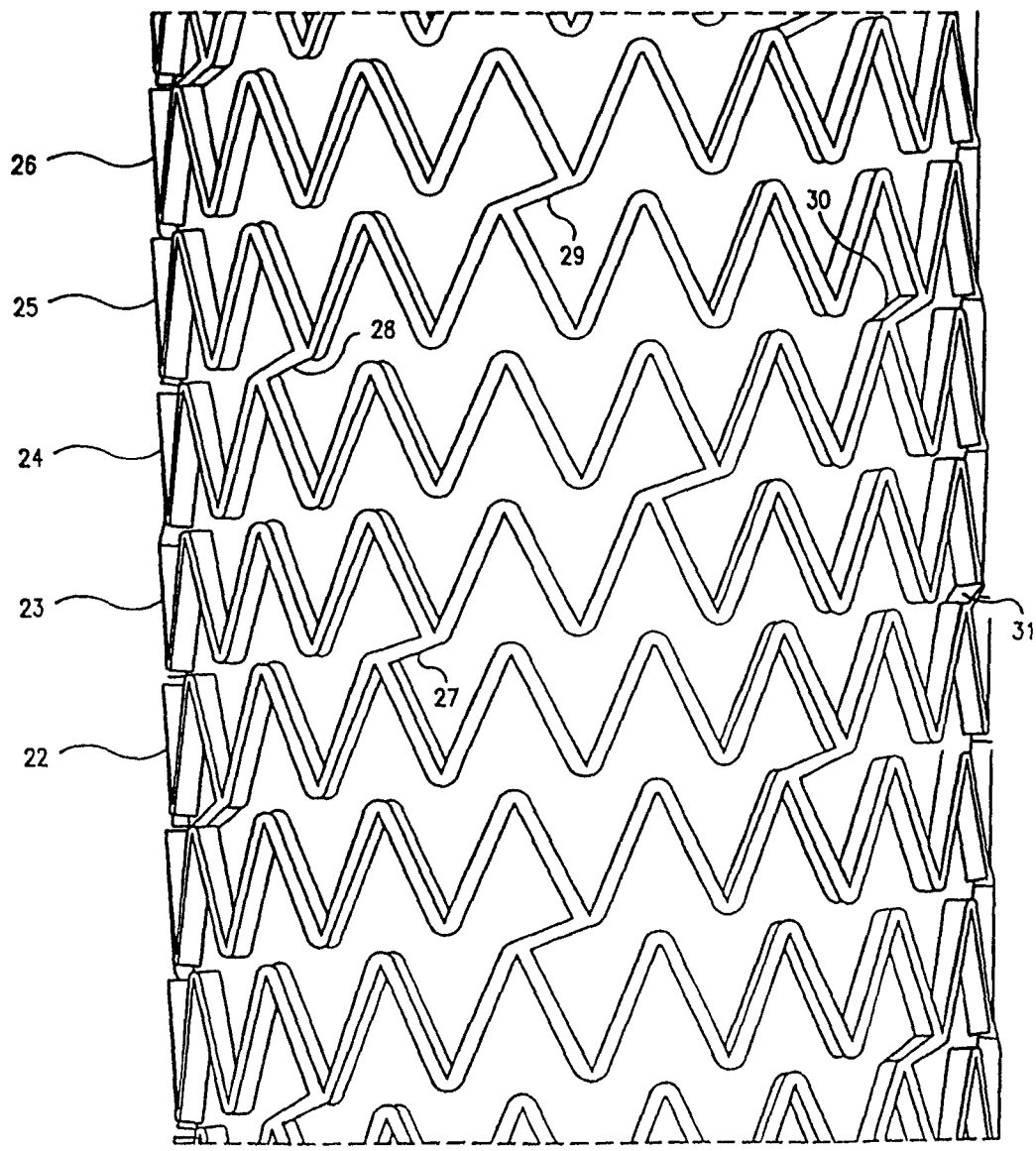
FIGS. 2 and 13 show close-up side-perspective views of the stents shown in FIGS. 1 and 12.
Figure 3:
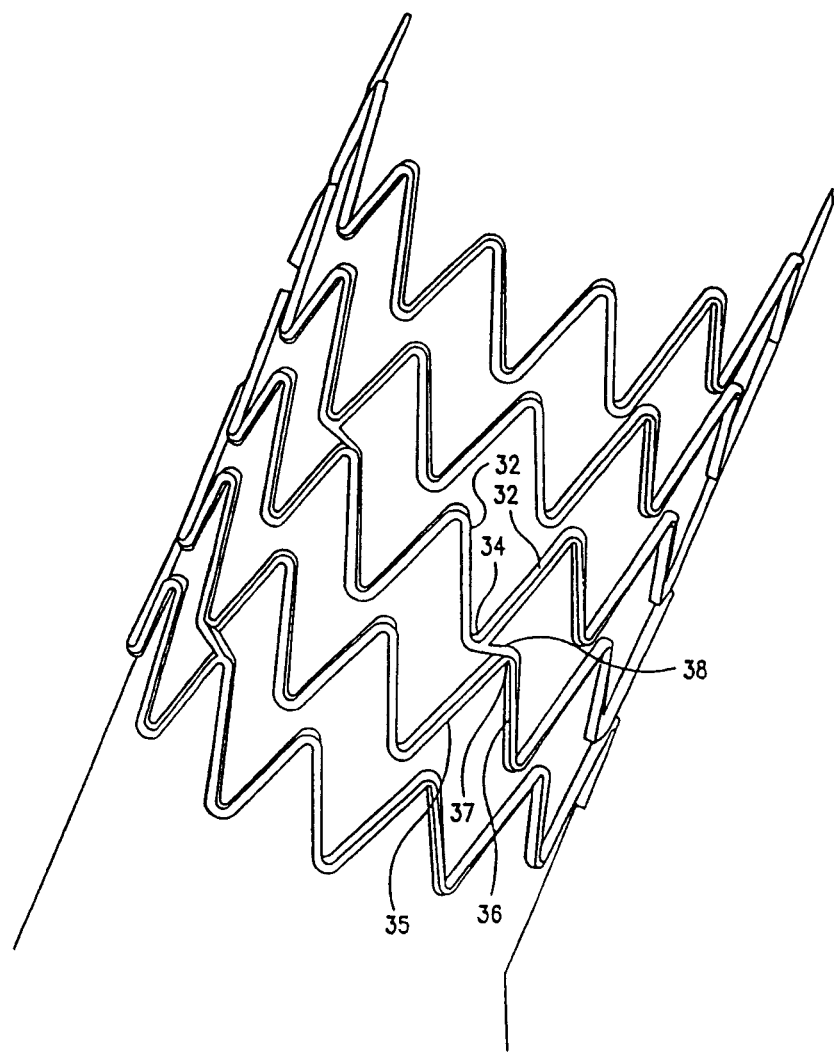
FIGS. 3 and 14 show an enlarged side-perspective view of several zigzag elements.
Figure 4:
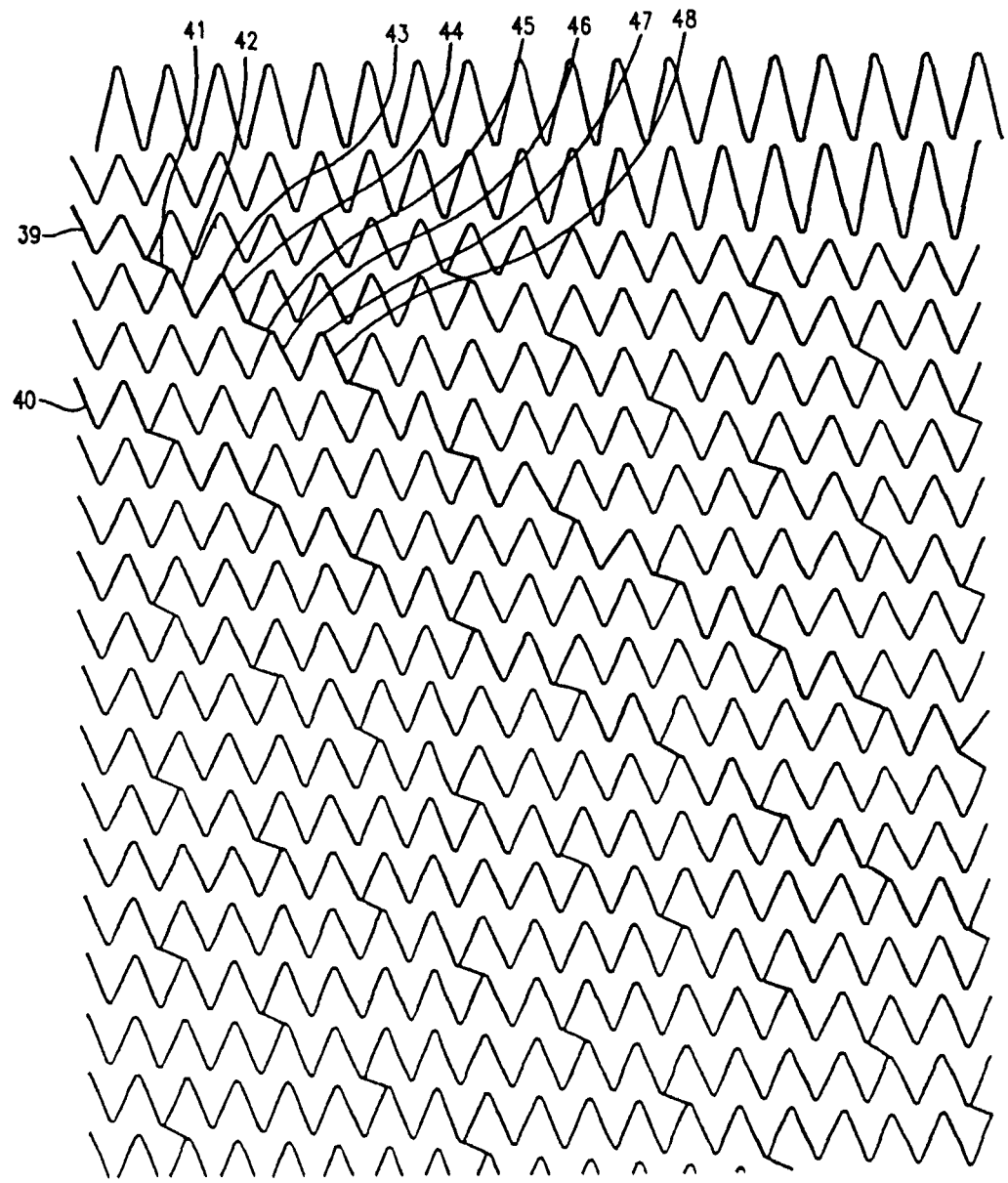
FIGS. 4 and 15 show a flattened perspective of the stent where the tube of the stent has been cut down the longitudinal axis and the stent laid flat.
Figure 5:
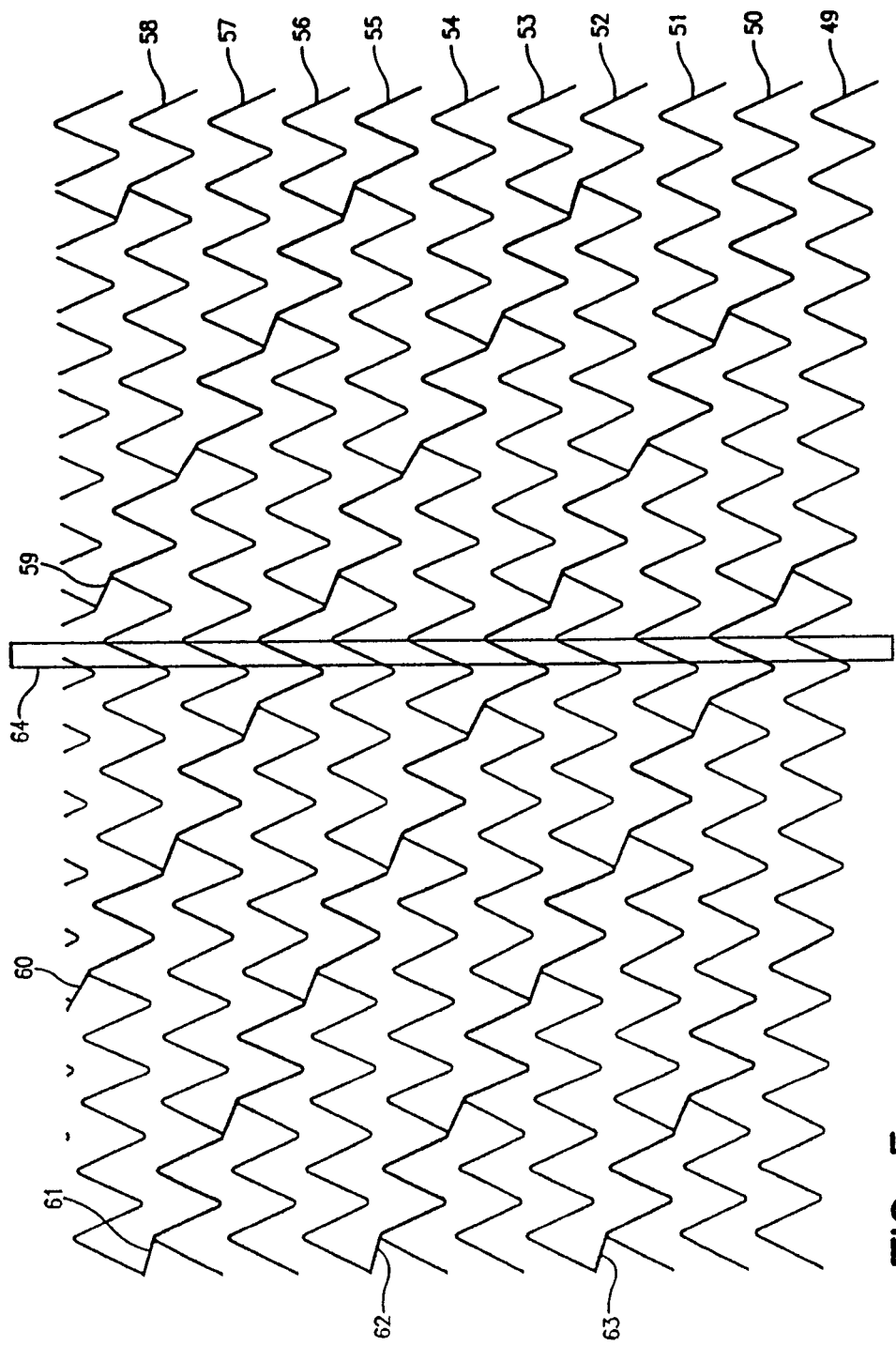
FIGS. 5 and 16 show the scaffolding lattice of the stent in a flattened perspective where the tube of the stent has been cut down the longitudinal axis and the stent laid flat.
Figure 6:
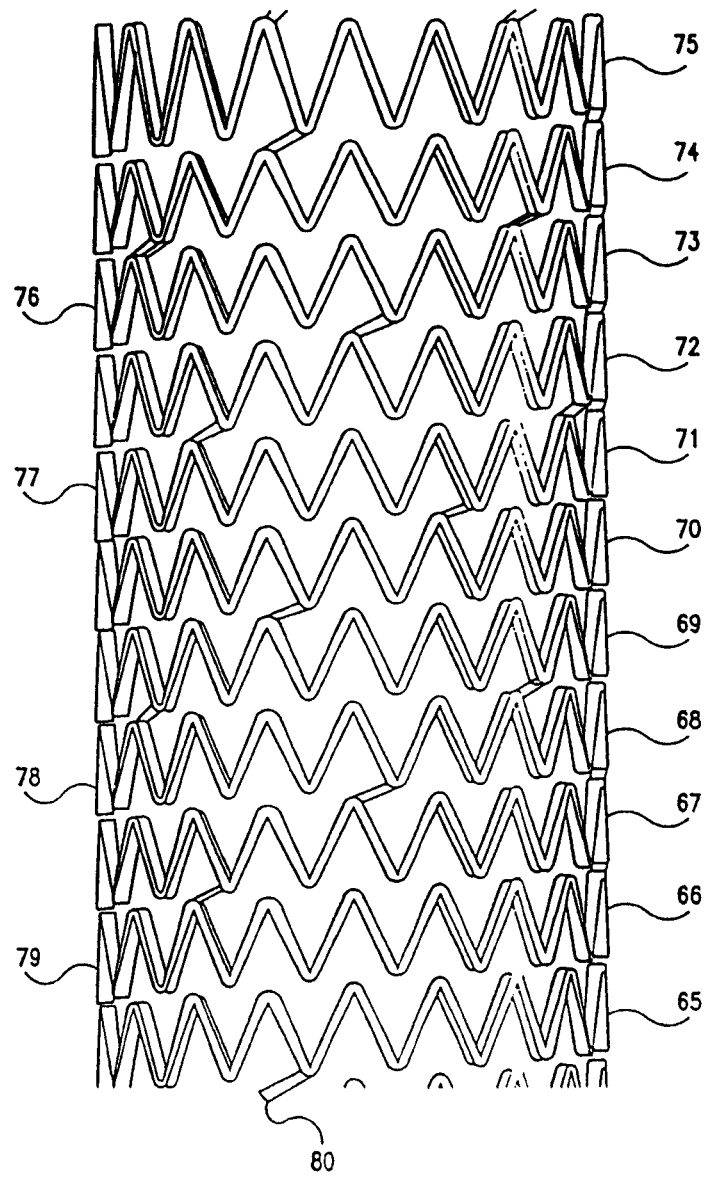
FIGS. 6 and 17 show a three-dimensional side-perspective of the stent illustrating the scaffolding lattice.
Figure 7:
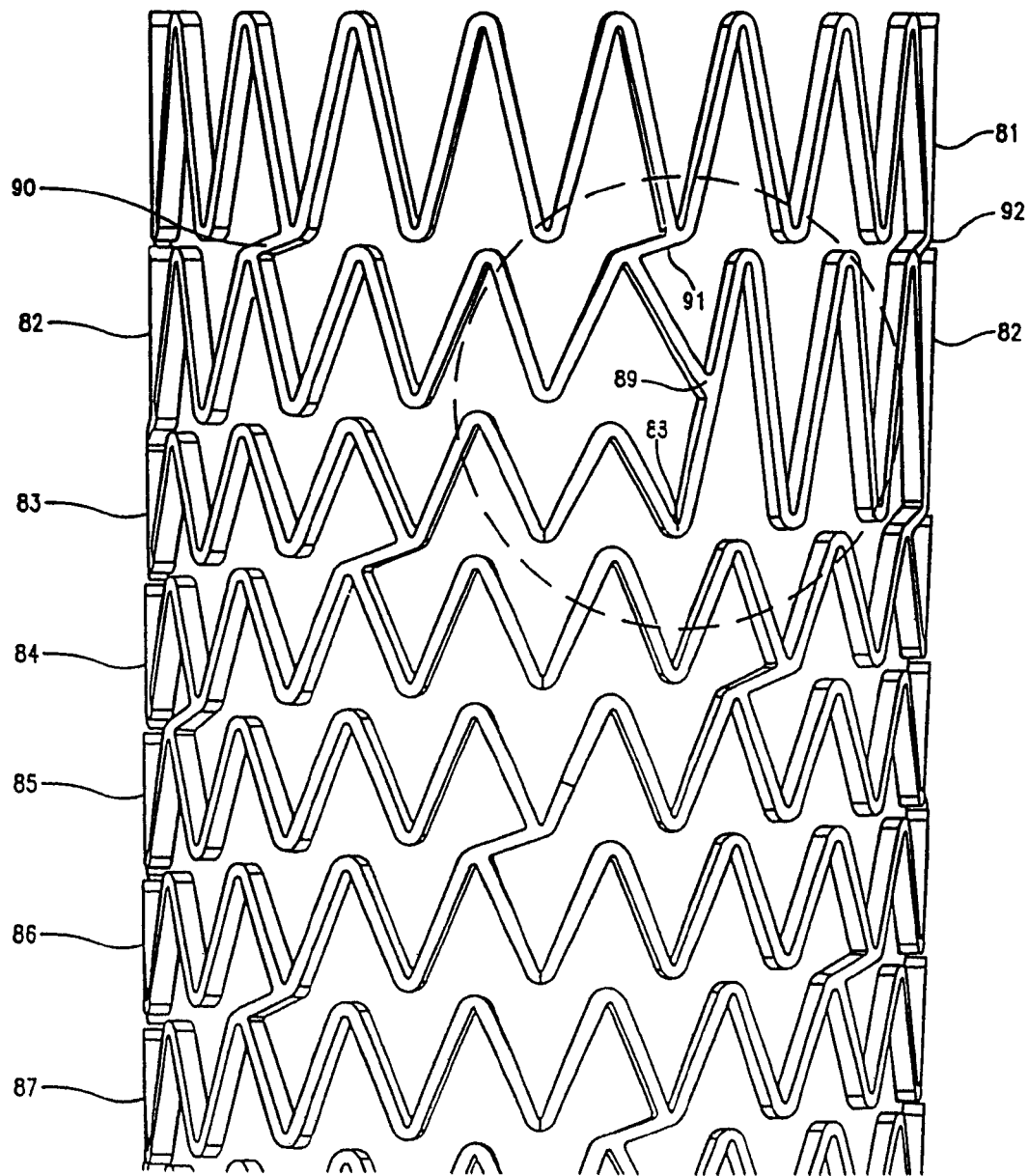
FIGS. 7 and 18 illustrate the closed circumferential element and the transition zone.
Figure 8:
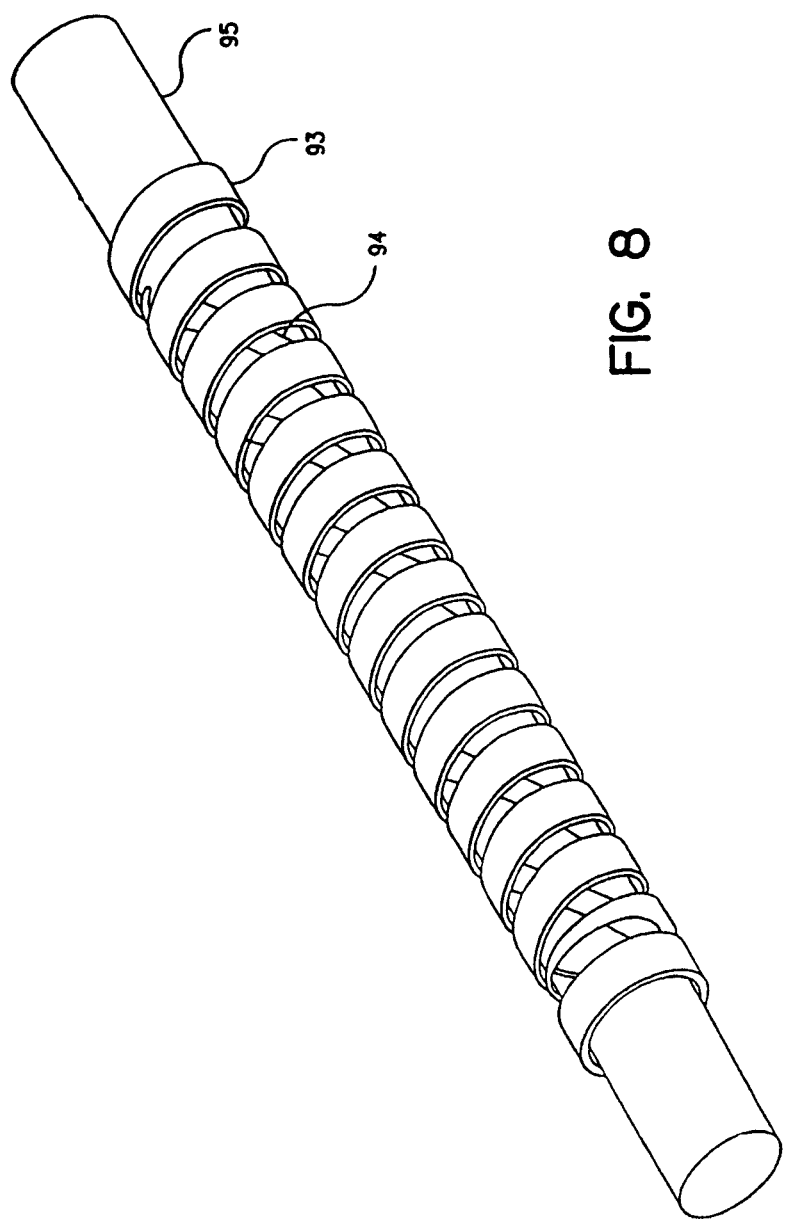
FIG. 8 shows a three-dimensional perspective of the scaffolding lattice of the stent formed by the two types of helices.
Figure 9:
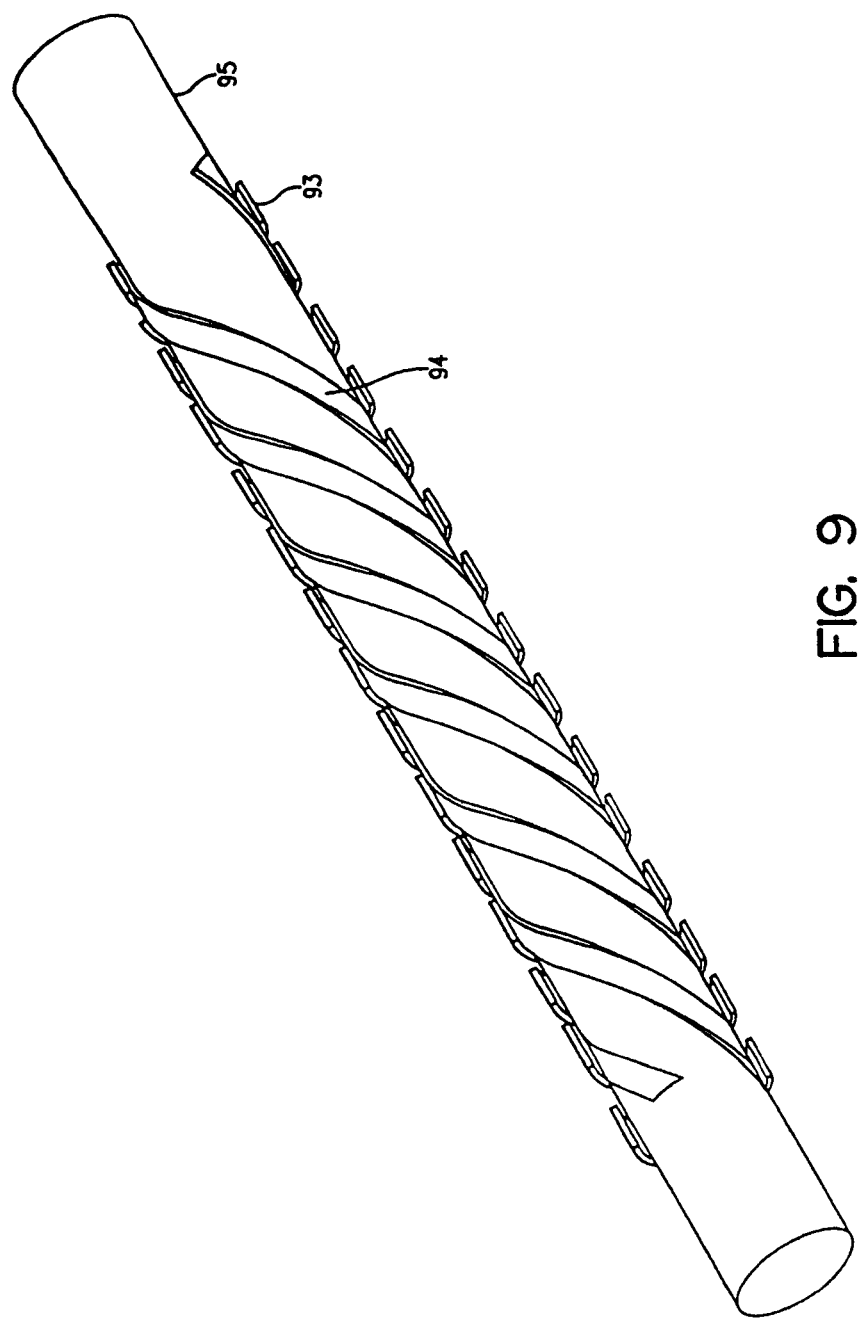
FIG. 9 shows a cutaway perspective of the stent in FIG. 8.

The scaffolding lattice of the stent formed by the two different types of helices is further illustrated in FIG. 8. The helix formed by the continuous zigzag elements is shown as 93. The helix formed by the connection elements is shown as 94. As is shown by the figures, the two different types of helices form a dual helical scaffolding lattice across the body of the stent. A cutaway perspective of the stent in FIG. 8 is shown in FIG. 9. The lumen of the blood vessel in which the stent is implanted is 95.

Figure 10:
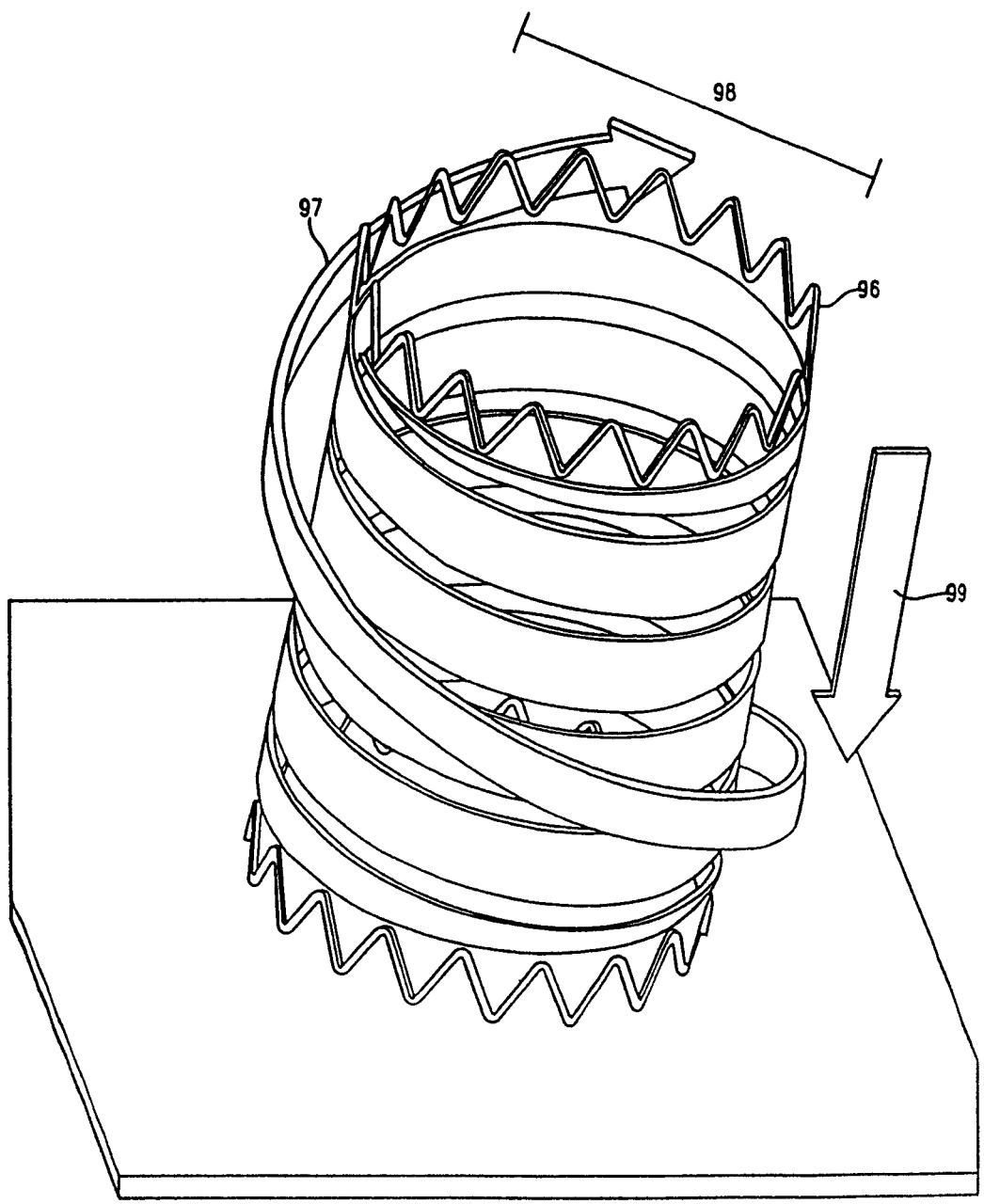
FIG. 10 illustrates how the stent contracts along the longitudinal axis.
Figure 11:
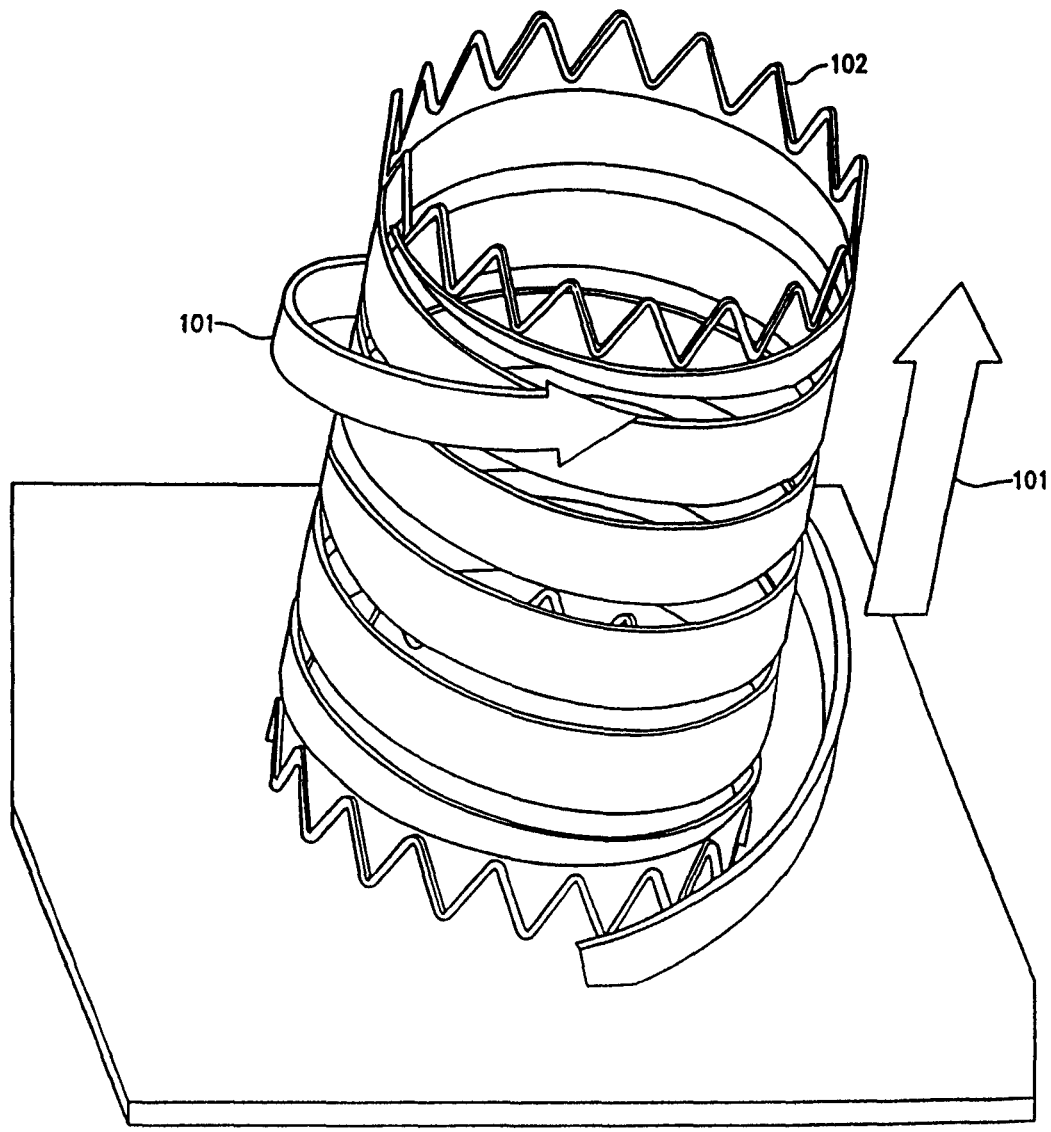
FIG. 11 illustrates how the stent expands along the longitudinal axis.

The scaffolding lattice uniformly supports the vessel wall while maintaining flexibility in a deployed state. This scaffolding lattice confers an anti-crushing property, such that when the stent is crushed radially the stent is capable of rapidly reestablishing its non-crushed state after the crushing force is removed. The scaffolding lattice also allows the stent of the invention to respond dynamically to physiological changes in the blood vessel such as longitudinal shrinkage of the vessel due to elastic recoil or vasconstriction. FIG. 10 illustrates how the stent contracts along the longitudinal axis 99. The stent 96 rotates clockwise 97. This results in contraction of the stent along the longitudinal axis 99. During longitudinal contraction 99, the stent maintains its un-contracted diameter 98. When the stent is rotated in the opposite direction counterclockwise 101, the stent 102 expands in a longitudinal direction 100 (see, FIG. 11 which illustrates expansion along the longitudinal axis). This expansion and contraction ability allows the stent to pulsate in response to changes in blood pressure. This dynamic response also prevents the stent of this invention from straightening the vessel in a non-physiological manner which can result in late term restenosis over the stented segment.

Composition and Formation of the Stent

The metal composition and process of formulating the stent is disclosed in U.S. Pat. No. 6,013,854 incorporated herein in its entirety by reference. The super elastic metal for the stent is preferably a super elastic alloy. A super elastic alloy is generally called "a shape-memory alloy" and resumes its original shape after being deformed to such a degree that an ordinary metal undergoes permanent deformation. Super elastic alloys useful in the invention include: Elgiloy.RTM. and Phynox.RTM. spring alloys (Elgiloy.RTM. alloy is available from Carpenter Technology Corporation of Reading Pa.; Phynox.RTM. alloy is available from Metal Imphy of Imphy, France), 316 stainless steel and MP35N alloy which are available from Carpenter Technology corporation and Latrobe Steel Company of Latrobe, Pa., and superelastic Nitinol nickel-titanium alloy which is available from Shape Memory Applications of Santa Clara, Calif. See, U.S. Pat. No. 5,891,191 to Stinson, incorporated herein in its entirety by reference.

The stent may be made, for example, by forming a pipe of a super elastic metal and then removing the parts of the pipe where the notches or holes are to be formed. As a result, the stent comprises a single piece without having any abrupt change in the physical property of the stent as would result from welding. The notches and holes can be formed in the pipe by laser (YAG laser, for example), electrical discharge, chemical etching, mechanical cutting, or a combined use of any of these techniques. See, U.S. Pat. No. 5,879,381 to Moriuchi et al., incorporated herein in its entirety by reference.

Having described several different embodiments of the invention, it is not intended that the invention is limited to such embodiments and that modifications and variations may be effected by one skilled in the art without departing from the spirit and scope of the invention as defined in the claims.

What is claimed is:

1. A self-expanding stent comprising a lattice, wherein the lattice comprises a first and a second helix forming a hollow tube having a longitudinal axis, wherein the first helix comprises a plurality of undulations, and the second helix comprises a plurality of elongate link connection elements in series with the undulations, wherein the connection elements connect fewer than all of the undulations in adjacent turns of the first helix and the number of undulations between consecutive connection elements in the second helix is 4, and further wherein the connection elements connect peak to valley of adjacent turns of the first helix and are positioned at an angle not parallel to the longitudinal axis of the stent, wherein the first and second helices proceed circumferentially in opposite directions along the entire longitudinal axis of the hollow tube, and wherein the first helix terminates in a transition zone formed by a plurality of undulations which have a closed loop at one end of the transition zone and connect to the undulations forming the first helix at the other end of the transition zone.

2. The self-expanding stent of claim 1, wherein each undulation is formed from ascending and descending arms connected together at a junction point.

3. The self-expanding stent of claim 2, wherein the connection element extends between the junction points lying on adjacent undulations.

4. The self-expanding stent of claim 3, wherein the number of connection elements in each 360-degree turn of the first helix is at least two.

5. The self-expanding stent of claim 4, wherein the number of connection elements in each 360-degree turn of the first helix is four.

6. The self-expanding stent of claim 1, wherein the undulations form a zigzag pattern.

7. The self-expanding stent of claim 1, wherein the undulations form a sinusoidal pattern.

8. The self-expanding stent of claim 1, wherein the amplitude of the undulations forming the transition zone increases as the undulations proceed circumferentially from the end forming the closed loop to the end connected to the first helix.

9. The self-expanding stent of claim 8, wherein the two ends of the transition zone are separated by at least one 360-degree turn of the first helix.

10. The self-expanding stent of claim 8, wherein the transition zone is linked by a plurality of connection elements to a closed circumferential element and the closed circumferential element is formed from a plurality of undulations.

11. The self-expanding stent of claim 10, wherein the undulations of the transition zone and the closed circumferential element have a sinusoidal pattern.

12. The self-expanding stent of claim 10, wherein the undulations of the transition zone and the closed circumferential element have a zigzag pattern.

13. The self-expanding stent of claim 10, wherein the closed circumferential element is radiopaque.

14. The self-expanding stent of claim 1, wherein the stent is composed of a nickel-titanium alloy.

15. A self-expanding stent comprising a lattice, wherein the lattice comprises a first and a second helix forming a hollow tube having a longitudinal axis, wherein each turn of the first helix comprises a plurality of zigzags and the second helix comprises a plurality of elongate link connection elements in series with the zigzags, wherein the connection elements connect fewer than all of the zigzags in adjacent turns of the first helix, and the number of undulations between consecutive connection elements in the second helix is 4, and further wherein the connection elements connect peak to valley of adjacent turns of the first helix and are positioned at an angle not parallel to the longitudinal axis of the stent, wherein the first and second helices proceed circumferentially in opposite directions along the entire longitudinal axis of the hollow tube, and wherein the first helix terminates in a transition zone formed by a plurality of zigzags which have a closed loop at one end of the transition zone and connect to the zigzags forming the first helix at the other end of the transition zone.

16. The self-expanding stent of claim 15, wherein each zigzag is formed from ascending and descending arms connected together at a junction point.

17. The self-expanding stent of claim 16, wherein the connection element extends between the junction points lying on adjacent zigzags.

18. The self-expanding stent of claim 17, wherein the number of connection elements in each 360-degree turn of the first helix is at least two.

19. The self-expanding stent of claim 18, wherein the number of connection elements in each 360-degree turn of the first helix is four.

20. The self-expanding stent of claim 15, wherein the amplitude of the zigzags forming the transition zone increases as the zigzags proceed circumferentially from the end forming the closed loop to the end connected to the first helix.

21. The self-expanding stent of claim 20, wherein the two ends of the transition zone are separated by at least one 360-degree turn of the first helix.

22. The self-expanding stent of claim 20, wherein the transition zone is linked by a plurality of connection elements to a closed circumferential element, wherein the closed circumferential element is formed from a plurality of zigzags.

23. The self-expanding stent of claim 22, wherein the closed circumferential element is radiopaque.

24. The self-expanding stent of claim 15, wherein the stent is composed of a nickel-titanium alloy.

25. A self-expanding stent comprising east one continuous first helix and a second helix; wherein each turn of the first helix comprises a plurality of zigzags and the second helix comprises a plurality of elongate link connection elements in series with the zigzags, wherein the connection elements connect fewer than all of the zigzags in adjacent turns of the first helix, and the number of undulations between consecutive connection elements in the second helix is 4, and further wherein the connection element connect peak to valley of adjacent turns of the first helix and are positioned at an angle not parallel to the longitudinal axis of the stent, wherein the first and second helices proceed circumferentially along the entire length of the stent in opposite directions to form a lattice in a tubular shape, and wherein the first helix terminates in a transition zone formed by a plurality of zigzags which have a closed loop at one end of the transition zone and connect to the zigzags forming the first helix at the other end of the transition zone.

26. The self-expanding stent of claim 25, wherein each zigzag is formed from ascending and descending arms connected together at a junction point.

27. The self-expanding stent of claim 25, wherein the amplitude of the zigzags forming the transition zone increases as the zigzags proceed circumferentially from the end forming the closed loop to the end connected to the first helix.

28. The self-expanding stent of claim 27, wherein the two ends of the transition zone are separated by at least one 360-degree turn of the first helix.

29. The self-expanding stent of claim 27, wherein the transition zone is linked by a plurality of connection elements to a closed circumferential element, wherein the closed circumferential element is formed from a plurality of zigzags.

30. The self-expanding stent of claim 29, wherein the closed circumferential element is radiopaque.

31. The self-expanding stent of claim 25, wherein the stent is composed of a nickel-titanium alloy.

32. A self-expanding stent comprising a lattice, wherein the lattice comprises a first and a second helix forming a hollow tube having a longitudinal axis, wherein each turn of the first helix comprises a plurality of zigzags and the second helix comprises a plurality of elongate link connection elements in series with the zigzags, wherein there are four connection elements in each turn of the first helix and the number of undulations between consecutive connection elements in the second helix is 4, and further wherein the connection elements connect peak to valley of adjacent turns of the first helix and are positioned at an angle not parallel to the longitudinal axis of the stent, wherein the first and second helices proceed circumferentially in opposite directions along the entire longitudinal axis of the hollow tube, and wherein the first helix terminates in a transition zone formed by a plurality of zigzags which have a closed loop at one end of the transition zone and connect to the zigzags forming the first helix at the other end of the transition zone.

* * * * *